United States Patent [19]

Shiga et al.

[11] Patent Number: 4,801,371

[45] Date of Patent: Jan. 31, 1989

[54] URANYL ION SELECTIVE ELECTRODE

[75] Inventors: Shujiro Shiga; Hideo Nagata; Kenichiro Shigeoka, all of Chiba, Japan

[73] Assignee: Sumitomo Chemical Co., Ltd., Osaka, Japan

[21] Appl. No.: 24,115

[22] Filed: Mar. 10, 1987

[30] Foreign Application Priority Data

Mar. 25, 1986 [JP] Japan .................................. 61-66943

[51] Int. Cl.$^4$ ........................................... G01N 27/30
[52] U.S. Cl. .................................................. 204/418
[58] Field of Search ................................. 204/418, 1 T

[56] References Cited

U.S. PATENT DOCUMENTS 3,864,233 2/1975 Dietrich et al. ..................... 204/418

Primary Examiner—G. L. Kaplan
Attorney, Agent, or Firm—Sughrue, Mion, Zinn, Macpeak & Seas

[57] ABSTRACT

A uranyl ion selective electrode having a responsive membrane, an inner reference electrode, and a uranyl ion inner solution is disclosed, in which the responsive membrane is obtained by treating a membrane material with an ion-exchanger comprising at least one uranyl ion complex formed between a uranyl ion and a neutral phosphoric ester or a neutral phosphorous ester as a complexing agent, a diluent excellent in compatibility with the ion-exchanger, and a solvent mediator having affinity for the membrane material. The electrode is excellent in concentration responsiveness, reproducibility, accuracy, and durability and is particularly suitable for use in uranyl ion analysis in the atomic energy industry.

15 Claims, No Drawings

URANYL ION SELECTIVE ELECTRODE

FIELD OF THE INVENTION

This invention relates to a uranyl ion selective electrode. More particularly, it relates to a uranyl ion selective electrode having a liquid ion-exchange membrane, which is excellent in concentration responsiveness, reproducibility, accuracy, and durability.

BACKGROUND OF THE INVENTION

With the recent development of the atomic energy industry, practical studies on electrodes for uranyl ion analysis that are essential to the atomic energy industry have been proceeded. With respect to uranyl ion selective electrodes of liquid ion-exchange membrane type, in which a uranyl ion inner solution at a fixed concentration is filled in the space between a reference electrode placed in the inner portion thereof and an outer tube, various reports have been made.

For example, it was reported in W. C. Dietrich, *Technical Progress Report*, No. Y1174D Y-12, Development Division (August–October, 1971) that a poly(vinyl chloride) (PVC) membrane containing a complex of di-(2-ethylhexyl) phosphate (D2EHP) and a uranyl ion is responsive to uranyl ions.

D. L. Manning et al. studied properties of PVC-based responsive membranes containing a uranyl ion complex formed with an acidic phosphoric ester using an acidic or neutral phosphonic ester or phosphoric ester as a diluent and proposed various kinds of PVC-based responsive membranes based on their study. However, a slope of potential response with respect to a common logarithmic concentration that is correlated to concentration responsiveness (hereinafter referred to as slope) of their responsive membranes was 26 mV/decade at the highest, that is smaller than the theoretical slope for divalent ions according to the Nernst equation (hereinafter referred to Nernstian slope (see *Anal. Chem.*, Vol. 46, No. 8, pp. 1116-1119 (1974)).

I. Goldberg et al. studied properties of PVC-based responsive membranes made of a uranyl ion complex formed with an acidic or neutral phosphoric ester, a phosphorous ester or an acidic phosphonic ester using any one of D2EHP, tributyl phosphate (TBP) and a variety of phosphonic esters as a diluent and obtained a slope close to the Nernstian slope from phosphorous ester type responsive membranes (see *Anal. Chem.*, Vo. 52, No. 13, pp 2105-2108 (1980)).

According to the above-cited reports, neither Manning et al. nor Goldberg et al. tried to mix PVC with a solvent mediator.

In general, electrodes having a greater slope exhibit higher performances as sensors. Any of the conventional responsive membranes as reported did not succeed to attain a slope greater than the Nernstian slope for divalent ions and are, therefore, still unsatisfactory for practical use as uranyl ion selective electrodes.

SUMMARY OF THE INVENTION

One object of this invention is to provide a uranyl ion selective electrode having a slope greater than the Nernstian slope.

As a result of extensive investigations, it has now been found that the above object can be accomplished by using a responsive membrane obtained by treating a membrane material with an ion-exchanger comprising at least one uranyl ion complex of a neutral phosphoric ester or a neutral phosphorous ester, a diluent having excellent compatibility with the ion-exchanger, and a solvent mediator having affinity for the membrane material.

That is, the present invention relates to a uranyl ion selective electrode having a responsive membrane, an inner reference electrode, and a uranyl ion inner solution, in which the responsive membrane is obtained by treating a membrane material with an ion-exchanger comprising at least one uranyl ion complex of a neutral phosphoric ester or a neutral phosphorous ester, a diluent excellent in compatibility with the ion-exchanger, and a solvent mediator having affinity for the membrane material.

DETAILED DESCRIPTION OF THE INVENTION

The uranyl ion selective electrode of the present invention is of a liquid ion-exchange membrane type. Liquid ion-exchange membrane type electrodes comprise an inner reference electrode, an outer tube, and a uranyl ion inner solution filled therebetween, the inner solution being in contact with a solution to be analyzed via a liquid ion-exchange membrane that constitutes a part of the outer tube.

The inner reference electrode which can be used in the present invention is conventional and includes, for example, a silver-silver chloride electrode, a calomel electrode, a mercury-mercurous sulfate electrode, etc.

The inner reference electrode to be used may be selected appropriately from commercially available electrodes without any restriction except that care should be taken upon use under exposure to radiation in the atomic energy industry. A key point of the present invention consists in the liquid ion-exchange membrane, which is required to show potential differences in good response to concentration difference through comparison with an outer reference electrode, and to have excellent reproducibility, accuracy (such as stability and response linearity) and durability and good ion selectivity.

The membrane material which can be used in the present invention is capable of forming a liquid ion-exchange membrane and suitably includes poly(vinyl acetate), silicone rubber, cellulose acetate, poly(vinyl chloride), epoxy resins, and the like, with poly(vinyl chloride) being particularly preferred.

Complexing agents which can be used for forming the ion-exchanger according to the present invention include neutral phosphoric esters and neutral phosphorous esters. These esters preferably include those containing an alkyl group or halogenated alkyl group having from 2 to 12 carbon atoms as an alkoxy group thereof. Examples of the alkyl or halogenated alkyl group having from 2 to 12 carbon atoms are an ethyl group, a propyl group, a butyl group, a hexyl group, an octyl group, a dodecyl group, and halogenated groups thereof. Of these, an alkyl group or halogenated alkyl group having from 3 to 8 carbon atoms is preferred.

Specific examples of the complexing agents to be used are tributyl phosphite, trioctyl phosphate, tri(-chloropropyl) phosphate, tri-(2-chloroethyl) phosphate, tri(chlorobutyl) phosphate, tri(chlorooctyl) phosphate, and the like. These may be used either alone or in combination thereof.

The diluent excellent in compatibility with the above-illustrated ion-exchangers preferably includes neutral phosphoric esters. The neutral phosphoric esters to be used preferably contain an alkyl group having from 2 to 12 carbon atoms as an alkoxy group thereof. Examples of such an alkyl group include an ethyl group, a propyl group, a butyl group, a hexyl group, an octyl group, a dodecyl group, etc., with those having from 3 to 8 carbon atoms being particularly preferred.

Specific examples of the diluents to be used are triethyl phosphate, tripropyl phosphate, tributyl phosphate, trihexyl phosphate, trioctyl phosphate, tridodecyl phosphate, etc. Of these, tributyl phosphate is preferred.

The solvent mediator having affinity for the membrane material (hereinafter simply referred to as solvent mediator) includes plasticizers and the like, such as phthalic esters, adipic esters, sebacic esters, glycol derivatives, etc. Among them, phthalic esters, adipic esters and sebacic esters are preferred. These esters preferably contain an alkyl group having from 2 to 12 carbon atoms as an alkoxy group thereof. Examples of such an alkyl group are an ethyl group, a propyl group, a butyl group, a heptyl group, a dodecyl group, etc., with an alkyl group having from 3 to 8 carbon atoms being preferred.

Specific examples of the solvent mediator are dioctyl phthalate (DOP), dioctyl adipate (DOA), dioctyl sebacate (DOS), etc.

The ion-exchanger is obtained by reacting uranyl nitrate hexahydrate with the complexing agent. The complexing agent is used in an amount of from 2 to 3 mols, preferably from 2.0 to 2.5 mols, per mol of the uranyl nitrate hexahydrate. A mixing ratio of the diluent to the solvent mediator ranges from 3/1 to $\frac{1}{3}$, preferably from 2/1 to $\frac{1}{2}$, by weight. The ion-exchanger formed from the complexing agent and uranyl nitrate is mixed with a mixture of the diluent and the solvent mediator at a mixing weight ratio of from 1/7 to 1/20 and preferably from $\frac{1}{8}$ to 1/15. The resulting mixture comprising the ion-exchanger, diluent, and solvent mediator is then mixed with the membrane material at such a mixing ratio that the proportion of the membrane material ranges from 20 to 50% by weight, preferably from 25 to 35% by weight, based on the total weight of the final mixture.

The process for treating the membrane material with the ion-exchanger comprising at least one uranyl ion complex of a neutral phosphoric ester or a neutral phosphorous ester, the diluent, and the solvent mediator to obtain a responsive membrane is not limited. For example, the treatment may be carried out by directly mixing the membrane material, ion-exchanger, diluent, solvent mediator, and the like, followed by heat-molding. In general, it is effected by dissolving the membrane material in a volatile good solvent such as tetrahydrofuran, cyclohexanone, etc., mixing the solution with the ion-exchanger, diluent, and solvent mediator or successively adding these components to the solution to form a uniform solution, and then removing the good solvent by evaporation.

The membrane preferably has a thickness of from 0.1 to 0.8 mm and more preferably of from 0.2 to 0.6 mm.

The uranyl ion inner solution can be prepared from uranyl nitrate or the like in a usual manner.

The present invention will now be illustrated in greater detail by way of the following examples, but it should be understood that the present invention is not limited thereto.

Procedures from preparation of a responsive membrane through measurement of a potential difference commonly employed in all test runs are described below.

(1) Preparation of PVC-Ion-Exchanger Responsive Membrane:

(a) Preparation of Ion-Exchanger:

To 1.00 g of uranyl nitrate hexahydrate is added a phosphoric ester (or a phosphorous ester) in an amount of from 2 to 3 mols per mol of uranyl nitrate hexahydrate. The mixture is well stirred and shaken until the solid phase of the uranyl nitrate has disappeared thereby to form a complex. In cases where an aqueous phase is formed as a lower layer, the mixture is subjected to separation by means of a centrifugal separator to completely separate the aqueous phase and the oily phase, and the aqueous phase is removed by the use of a syringe, etc. The remaining viscous yellow liquid (oily phase) is a complex formed between the phosphoric ester (or the phosphorous ester) and the uranyl nitrate.

Two 100 mg portions of anhydrous sodium sulfate are added to the liquid. After addition of each portion, the mixture is centrifuged to remove the solid phase and dried. The thus prepared ion-exchanger (complex) is preserved in a dried test tube equipped with a cap.

(b) Preparation of Responsive Membrane:

The ion-exchanger weighing 45 mg and a mixed solvent (consisting of a diluent and a solvent mediator) weighing 400 mg are placed in a dried 50 to 100 ml-volume beaker (weight ratio of ion-exhanger/mixing solvent=about 1/9), and the mixture is well stirred. The weight ratio of the diluent to the solvent mediator is 1/1. In some test runs, the solvent mediator is not used. Such being the case, 400 mg of a diluent is used alone. To the resulting solution is added 6 ml of a solution of 1.75 g of PVC (SX-DH made by Sumitomo Chemical Co., Ltd.; viscosity average polymerization degree: 2620) in 60 ml of tetrahydrofuran (THF), followed by thoroughly stirring. The resulting solution is poured into a petri dish having a diameter of about 30 mm, which is then covered with 2 or 3 sheets of filter paper and allowed to stand horizontally in a draft chamber thereby to gradually evaporate THF over a period of at least 36 hours.

(2) Assembly of Electrode:

The dried PVC-based responsive membrane is cut into a disk having a diameter of 12 mm by means of a cork borer, a cutter, etc., and adhered to one end of a PVC tube having an outer diameter of 12 mm and a length of from 30 to 40 mm with an adhesive prepared by dissolving 7 g of PVC in 60 ml of THF. After the adhesive has thoroughly been dried, the responsive membrane is conditioned by contacting both sides of the PVC responsive membrane with a $10^{-2}$M uranyl nitrate solution by immersion for at least 24 hours and desirably for 72 hours or more, before using it. In the case where the responsive membrane is preserved apart from the inner electrode, it is similarly immersed in a $10^{-2}$M uranyl nitrate solution.

In assembling into an electrode, the PVC tube with the responsive membrane adhered to one end thereof is fixed to the end of a silver-silver chloride reference electrode with a sealing tape. A $10^{-2}$M uranyl nitrate solution (pH=3.0) is filled in the space between the responsive membrane and the reference electrode in advance. Accordingly, the resulting electrode (indicator electrode) has a structure as illustrated below.

Ag/AgCl, KCl ‖ UO$_2$(NO$_3$)$_2$, 10$^{-2}$M (pH = 3) |membrane|

(Inner Reference   (Inner Solution)
  Electrode)

(3) Preparation of Uranyl Nitrate Aqueous Solution Having Standard Concentration:

A uranyl ion standard solution at a concentration of 10$^{-1}$M, 10$^{-2}$M, 10$^{-3}$M, or 10$^{-4}$M is prepared. Prior to the potential difference measurements, the solution is adjusted to a pH of 3.0 with a 1N HNO$_3$ or 1N KOH solution.

(4) Measurement of Potential Difference:

A cell is assembled from the above obtained indicator electrode and, as an outer reference electrode, the same electrode as used in the indicator electrode as the inner reference electrode. The electromotive force (potential difference) of the cell is measured at 25°±2° C. by means of a pH/mV meter (F-8AT model, manufactured by Horiba Co., Ltd.). A sample solution in a beaker is gently stirred by a magnetic stirrer, while preventing temperature rise by sandwiching a heat-insulating mat between the beaker and the stirrer. The point where a potential change in 10 minutes decreases to 1 mV or less is read off as a determinate potential at the concentration of the sample solution.

COMPARATIVE EXAMPLE 1

A ion-exchanger was prepared in accordance with the procedure as described in (1)-(a) by using dibutyl phosphate (DBP) (Run No. 1) or D2EHP (Run No. 2), which is a typical conventional complexing agent, in an amount double the molar quantity of uranyl ions. A responsive membrane was prepared in accordance with the procedure of (1)-(b) above by using the resulting ion-exchanger and TBP as a diluent but using no solvent mediator, and then assembled into a cell.

The performance properties of the above prepared responsive membrane were evaluated by measuring potential differences at a varying uranyl ion concentration, and the results obtained are shown in Table 1.

TABLE 1

| Responsive Membrane: | Run No. 1 | | Run No. 2 | |
|---|---|---|---|---|
| Complexing Agent | DBP | | D2EHP | |
| Diluent | TBP | | TBP | |
| Solvent Mediator | none | | none | |
| Uranyl Ion Concn. (M) | Potential Difference (mV) | Slope (mV/decade) | Potential Difference (mV) | Slope (mV/decade) |
| 10$^{-4}$ | −68.3 | | −43.5 | |
| | | 29.4 | | 33.0 |
| 10$^{-3}$ | −38.9 | | −10.5 | |
| | | 19.3 | | 9.5 |
| 10$^{-2}$ | −19.6 | | −1.0 | |
| | | 21.0 | | 9.1 |
| 10$^{-1}$ | 1.4 | | 8.1 | |
| | | 25.7 | | 9.9 |
| 10$^{-2}$ | −24.3 | | −1.8 | |
| | | 35.1 | | 22.2 |
| 10$^{-3}$ | −59.4 | | −24.0 | |
| | | 26.5 | | −0.9 |
| 10$^{-4}$ | −85.9 | | −23.1 | |

Making a review on potential difference in view of uranyl ion concentration, the Nernstian slope for divalent ions can be obtained in some cases, and response linearity is established within a certain concentration range. The potential difference is stable and becomes constant in a short period of time without fluctuations. The test was conducted from the top of Table 1 downward. That is, measurements were made starting from the lowest concentration to the highest concentration, and then reverting to the lowest one. In the case of using D2EHP as a complexing agent, the reproducibility along this variation in concentration is very poor, and the membrane does not substantially respond to uranyl ion concentrations no higher than 10$^{-3}$M.

EXAMPLE 1

Responsive membranes were prepared using tributyl phosphite as a complexing agent and DOA (dioctyl adipate) or DOS (dioctyl sebacate) as a solvent mediator, and their performance properties were evaluated. The results obtained are shown in Table 2.

TABLE 2

| Responsive Membrane: | Run No. 3 | | Run No. 4 | |
|---|---|---|---|---|
| Complexing Agent | tributyl phosphite | | tributyl phosphite | |
| Diluent | TBP | | TBP | |
| Solvent Mediator | DOA | | DOS | |
| Uranyl Ion Concn. (M) | Potential Difference (mV) | Slope (mV/decade) | Potential Difference (mV) | Slope (mV/decade) |
| 10$^{-4}$ | −70.7 | | −84.5 | |
| | | 40.7 | | 39.2 |
| 10$^{-3}$ | −30.0 | | −45.5 | |
| | | 42.1 | | 42.0 |
| 10$^{-2}$ | 12.1 | | −3.5 | |
| | | 18.1 | | 41.3 |
| 10$^{-1}$ | 30.2 | | 37.8 | |
| | | 22.8 | | 43.6 |

TABLE 2-continued

| | | | | |
|---|---|---|---|---|
| $10^{-2}$ | 7.4 | | −5.8 | |
| | | 34.7 | | 39.2 |
| $10^{-3}$ | −27.3 | | −45.0 | |
| | | 36.0 | | 46.1 |
| $10^{-4}$ | −63.3 | | −91.1 | |

EXAMPLE 2

Responsive membranes were prepared by using tri(chloropropyl) phosphate as a complexing agent and DOP (dioctyl phthalate) or DOA as a solvent mediator. Performance properties of the resulting responsive membranes were evaluated, and the results obtained are shown in Table 3.

TABLE 3

| Responsive Membrane: | Run No. 5 | | Run No. 6 | |
|---|---|---|---|---|
| Complexing Agent | tri(chloropropyl) phosphate | | tri(chloropropyl) phosphate | |
| Diluent | TBP | | TBP | |
| Solvent Mediator | DOP | | DOA | |
| Uranyl Ion Concn. (M) | Potential Difference (mV) | Slope (mV/decade) | Potential Difference (mV) | Slope (mV/decade) |
| $10^{-4}$ | −81.1 | | −73.6 | |
| | | 38.5 | | 19.7 |
| $10^{-3}$ | −42.6 | | −53.9 | |
| | | 49.4 | | 57.4 |
| $10^{-2}$ | 6.8 | | 3.5 | |
| | | 28.0 | | 27.2 |
| $10^{-1}$ | 34.8 | | 30.7 | |
| | | 26.1 | | 34.3 |
| $10^{-2}$ | 8.7 | | −3.6 | |
| | | 47.5 | | 52.9 |
| $10^{-3}$ | −38.8 | | −56.5 | |
| | | 41.0 | | 17.7 |
| $10^{-4}$ | −79.8 | | −74.2 | |

EXAMPLE 3

Responsive membranes were prepared by using trioctyl phosphate as a complexing agent and DOP, DOA, or DOS as a solvent mediator. Performance properties of the resulting responsive membranes were evaluated, and the results obtained are shown in Table 4.

dance with the present invention. It can be seen that the slope of these electrodes are obviously improved. Seeing that the Nernstian slope for monovalent ions ranges from about 59 to 60 mV/decade, the uranyl ions are regarded to have an electrical charge intermediate between monovalent ions and divalent ions according to the liquid ion-exchange membrane of the present invention. Further, there is obtained response linearity in the main concentration range, which would extend the applicable range of concentration where good reproducibility can be obtained.

COMPARATIVE EXAMPLE 2

A responsive membrane was prepared in the same manner as in Comparative Example 1 except that DOP

TABLE 4

| Responsive Membrane: | Run No. 7 | | Run No. 8 | | Run No. 9 | |
|---|---|---|---|---|---|---|
| Complexing Agent | trioctyl phosphate | | trioctyl phosphate | | trioctyl phosphate | |
| Diluent | TBP | | TBP | | TBP | |
| Solvent Mediator | DOP | | DOA | | DOS | |
| Uranyl Ion Concn. (M) | Potential Difference (mV) | Slope (mV/decade) | Potential Difference (mV) | Slope (mV/decade) | Potential Difference (mV) | Slope (mV/decade) |
| $10^{-4}$ | −77.5 | | −85.6 | | −78.5 | |
| | | 21.0 | | 28.2 | | 33.0 |
| $10^{-3}$ | −56.5 | | −57.4 | | −45.5 | |
| | | 46.7 | | 46.6 | | 43.8 |
| $10^{-2}$ | −9.8 | | −10.8 | | −1.7 | |
| | | 33.6 | | 45.7 | | 35.1 |
| $10^{-1}$ | 23.8 | | 34.9 | | 33.4 | |
| | | 35.8 | | 45.4 | | 30.1 |
| $10^{-2}$ | −12.0 | | −10.5 | | 3.3 | |
| | | 44.7 | | 45.4 | | 44.7 |
| $10^{-3}$ | −56.7 | | −55.9 | | −41.4 | |
| | | 41.1 | | 29.2 | | 34.3 |
| $10^{-4}$ | −97.8 | | −85.1 | | −75.7 | |

A review on Tables 2 to 4 is presented below. These tables show results of electrodes prepared in accordance was added as a solvent mediator in each case. The results of evaluations are shown in Table 5.

TABLE 5

| Responsive Membrane: | Run No. 10 | | Run No. 11 | |
|---|---|---|---|---|
| Complexing Agent | DBP | | D2EHP | |
| Diluent | TBP | | TBP | |
| Solvent Mediator | DOP | | DOP | |
| Uranyl Ion Concn. (M) | Potential Difference (mV) | Slope (mV/decade) | Potential Difference (mV) | Slope (mV/decade) |
| $10^{-4}$ | −21.0 | | −51.3 | |
| | | 10.6 | | 31.7 |
| $10^{-3}$ | −10.4 | | −19.6 | |
| | | 5.1 | | 17.0 |
| $10^{-2}$ | −5.3 | | −2.6 | |
| | | −7.3 | | 23.4 |
| $10^{-1}$ | −12.6 | | 20.8 | |
| | | −9.6 | | 17.9 |
| $10^{-2}$ | −3.0 | | 2.9 | |
| | | −6.9 | | 19.7 |
| $10^{-3}$ | 3.9 | | −16.8 | |
| | | 34.1 | | 36.8 |
| $10^{-4}$ | −30.2 | | −53.6 | |

It can be seen from Table 5 that the reproducibility and response linearity of the responsive membrane of Run No. 11 are considerably improved over those of Run No. 2 of Comparative Example 1. In the case of using DBP as a complexing agent, both the reproducibility and response linearity become worse as compared with Run No. 1 of Comparative Example 1. It is noteworthy that the system using DBP or D2EHP as a complexing agent cannot attain a slope greatly exceeding the Nernstian slope for divalent ions irrespective of whether a solvent mediator is added or not.

COMPARATIVE EXAMPLE 3

A responsive membrane was prepared in the same manner as in Example 1 except for using no solvent mediator. The results of evaluations are shown in Table 6.

TABLE 6

| | Run No. 12 | |
|---|---|---|
| Uranyl Ion Concn. (M) | Potential Difference (mV) | Slope (mV/decade) |
| $10^{-4}$ | −55.2 | |
| | | 13.6 |
| $10^{-3}$ | −41.6 | |
| | | 31.7 |
| $10^{-2}$ | −9.9 | |
| | | 18.4 |
| $10^{-1}$ | 8.5 | |
| | | 18.4 |
| $10^{-2}$ | −9.9 | |
| | | 29.2 |
| $10^{-3}$ | −39.1 | |
| | | 22.1 |
| $10^{-4}$ | −61.2 | |

COMPARATIVE EXAMPLE 4

A responsive membrane was prepared in the same manner as in Example 2 except for using no solvent mediator. The results of evaluations are shown in Table 7.

TABLE 7

| | Run No. 13 | |
|---|---|---|
| Uranyl Ion Concn. (M) | Potential Difference (mV) | Slope (mV/decade) |
| $10^{-4}$ | −51.5 | |
| | | 7.7 |
| $10^{-3}$ | −43.8 | |
| | | 37.8 |
| $10^{-2}$ | −6.0 | |
| | | 21.0 |
| $10^{-1}$ | 15.5 | |
| | | 16.0 |
| $10^{-2}$ | −1.0 | |
| | | 49.5 |
| $10^{-3}$ | −50.5 | |
| | | 15.9 |
| $10^{-4}$ | −66.4 | |

COMPARATIVE EXAMPLE 5

A responsive membrane was prepared in the same manner as in Example 3 except for using no solvent mediator. The results of evaluations are shown in Table 8.

TABLE 8

| | Run No. 14 | |
|---|---|---|
| Uranyl Ion Concn. (M) | Potential Difference (mV) | Slope (mV/decade) |
| $10^{-4}$ | −22.2 | |
| | | 4.5 |
| $10^{-3}$ | −17.7 | |
| | | 23.8 |
| $10^{-2}$ | 6.1 | |
| | | 15.7 |
| $10^{-1}$ | 21.8 | |
| | | 12.6 |
| $10^{-2}$ | 9.2 | |
| | | 23.4 |
| $10^{-3}$ | −14.2 | |
| | | 11.8 |
| $10^{-4}$ | −26.0 | |

COMPARATIVE EXAMPLE 6

Responsive membranes were prepared in the same manner as in Examples 1 to 3 except for replacing the whole amount of the respective diluent with the same amount of the respective solvent mediator. When these membranes were subjected to potentiometry, the pointer of the potentiometer fluctuated with an amplitude of several millivolts at several frequencies per second with no exception. All these membranes were opaque, and it was revealed by observation under an electron probe microanalyzer (EPMA) that the uranyl ion complex had an isolated structure, indicating poor dispersing quality.

In general, sensitive membranes are transparent, whereas insensitive membranes are semi-transparent to opaque as observed in Comparative Example 6. These facts suggest that the properties of co-existing diluents and solvent mediators play a very important role in manifestation of electrochemical characteristics of the uranyl ion complex. It should be understood, however, that the present invention is not limited by the above-described morphological observations.

Reverting to Comparative Examples 3 to 5 where the whole amount of the solvent mediator used in the corresponding Examples 1 to 3 was replaced with the respective diluent, it is obvious that the slope obtained approached close to the Nernstian slope for divalent ions. To the contrary, in Comparative Example 6 where the whole amount of TBP used as a diluent in the corresponding Examples 1 to 3 was replaced with the respective solvent mediator, all the membranes showed fluctuations in potential difference measurement as described above. The plasticizers, i.e., DOP, DOA, and DOS, are capable of dissolving uranyl ion complexes, though the rate of dissolution is low. Nevertheless, the electrodes have extremely inferior performances as ion-selective electrodes unless these solvent mediators are employed in a mixed solvent with the diluent.

In order to elucidate causes of such a difference in performance properties of responsive membranes, the samples prepared in Examples and Comparative Examples were observed under an optical microscope, a scanning electron microscope (SEM), and EPMA. As a result, no distinct difference between the membranes of Examples and those of Comparative Examples was noted through observations under an optical microscope or SEM, but the observation by EPMA proved that membranes of the present invention are superior in dispersed state of the uranyl ion complex as compared with the comparative ones.

EXAMPLE 4

The same procedure as in Run No. 3 of Example 1 was repeated except that the uranyl nitrate test solution contained zirconyl nitrate at a zirconyl ion concentration of $5 \times 10^{-4}$M as an interfering ion (the solution had a pH of 3.0). The results of evaluation are shown in Table 9.

TABLE 9

| Uranyl Ion Concn. (M) | Run No. 15 Slope (mV/decade) |
|---|---|
| $10^{-4}$ | |
| | 14.3 |
| $10^{-3}$ | |
| | 46.6 |
| $10^{-2}$ | |
| | 30.7 |
| $10^{-1}$ | |
| | 27.2 |
| $10^{-2}$ | |
| | 43.6 |
| $10^{-3}$ | |
| | 17.9 |

TABLE 9-continued

| Uranyl Ion Concn. (M) | Run No. 15 Slope (mV/decade) |
|---|---|
| $10^{-4}$ | |

The data of Table 9 show ion selectivity of the membrane of Example 1. It can be seen that the dilute uranyl nitrate solution having a uranyl ion concentration not more than $10^{-3}$M undergoes influences of zirconyl ions even at a low zirconyl ion concentration of $5 \times 10^{-4}$M.

EXAMPLE 5

The same procedure of Example 4 was repeated except for replacing zirconyl nitrate with cerium (III) nitrate so as to have a cerium ion concentration of $10^{-3}$M. The results of evaluation are shown in Table 10.

TABLE 10

| Uranyl Ion Concn. (M) | Run No. 16 Slope (mV/decade) |
|---|---|
| $10^{-4}$ | |
| | 29.7 |
| $10^{-3}$ | |
| | 47.4 |
| $10^{-2}$ | |
| | 39.7 |
| $10^{-1}$ | |
| | 38.4 |
| $10^{-2}$ | |
| | 42.2 |
| $10^{-3}$ | |
| | 30.8 |
| $10^{-4}$ | |

Making a comparison betweeen Tables 9 and 10, it can be seen that a cerium ion has weaker influences than a zirconyl ion. Both zirconyl and cerium ions are important components in the nuclear fuel reprocessing waste liquor in view of their amounts as well as their electrochemical activities. The above-recited reference of Goldberg et al. describes cases where the selective coefficient of cerium (IV) exceeds 3. The selective coefficient of the responsive membranes obtained in this Example is about 0.01, indicating that they are comparable to the conventional membranes.

EXAMPLE 6

In order to examine influences of hydrogen ion concentration on responsive membranes, performance properties of the membrane of Run No. 3 of Example 1 were evaluated with a pH of the test solution being varied. The results obtained are shown in Table 11.

Of interfering ions, hydrogen ions exert the greatest influences on performances of membranes as shown in Table 11. Therefore, control of hydrogen ion concentration is inevitable in this kind of electrode for assuring accuracy of quantitative determination, as mentioned also in the reference of Manning et al.

TABLE 11

| | Run No. 17 | Run No. 18 | Run No. 19 | Run No. 20 | Run No. 21 |
|---|---|---|---|---|---|
| H$^+$ Concn. (pH) | 2.0 | 2.5 | 3.0 | 3.5 | 4.0 |
| Uranyl Ion Concn. (M): | | | Slope (mV/decade) | | |
| $10^{-4}$ | | | | | |
| | 8.2 | 34.6 | 40.9 | 52.9 | 45.9 |

TABLE 11-continued

| $10^{-3}$ | | | | | |
|---|---|---|---|---|---|
| | 42.0 | 50.5 | 51.8 | 47.6 | 30.1 |
| $10^{-2}$ | | | | | |
| | 57.0 | 60.3 | 38.0 | 26.7 | — |
| $10^{-1}$ | | | | | |
| | 56.8 | 58.8 | 37.8 | 27.9 | — |
| $10^{-2}$ | | | | | |
| | 40.6 | 50.7 | 50.9 | 47.1 | 30.9 |
| $10^{-3}$ | | | | | |
| | 16.8 | 37.4 | 42.5 | 49.0 | 44.7 |
| $10^{-4}$ | | | | | |

EXAMPLE 7

In order to evaluate durability, the electrode of Run No. 3 or Example 1 was immersed in a $10^{-2}$M solution of uranyl nitrate (pH=3.0) for a prescribed period of time and then measured for potential difference. Table 12 shows the results obtained for the sample immediately after the preparation and the sample having been immersed for 20 days.

TABLE 12

| | Run No. 22 | Run No. 23 |
|---|---|---|
| Responsive Membrane: | | |
| Complexing Agent | tributyl phosphite | tributyl phosphite |
| Diluent | TBP | TBP |
| Solvent Mediator | DOA | DOA |
| Immersion Time (day) | 0 | 20 |
| Uranyl Ion Concn. (M) | Slope (mV/decade) | Slope (mV/decade) |
| $10^{-4}$ | | |
| | 40.7 | 32.8 |
| $10^{-3}$ | | |
| | 42.1 | 40.9 |
| $10^{-2}$ | | |
| | 18.1 | 43.2 |
| $10^{-1}$ | | |
| | 22.8 | 45.2 |
| $10^{-2}$ | | |
| | 34.7 | 34.6 |
| $10^{-3}$ | | |
| | 36.0 | 36.4 |
| $10^{-4}$ | | |

EXAMPLE 8

The same test as in Example 7 was conducted for the electrode of Run No. 4 of Example 1. The results obtained are shown in Table 13.

TABLE 13

| | Run No. 24 | Run No. 25 |
|---|---|---|
| Responsive Membrane: | | |
| Complexing Agent: | tributyl phosphite | tributyl phosphite |
| Diluent | TBP | TBP |
| Solvent Mediator | DOS | DOS |
| Immersion Time (day) | 0 | 31 |
| Utanyl Ion Concn. (M) | Slope (mV/decade) | Slope (mV/decade) |
| $10^{-4}$ | | |
| | 39.2 | 34.6 |
| $10^{-3}$ | | |
| | 42.0 | 43.5 |
| $10^{-2}$ | | |
| | 41.3 | 45.1 |
| $10^{-1}$ | | |
| | 43.6 | 45.6 |
| $10^{-2}$ | | |
| | 39.2 | 43.2 |
| $10^{-3}$ | | |

TABLE 13-continued

| | | |
|---|---|---|
| | 46.1 | 37.6 |
| $10^{-4}$ | | |

EXAMPLE 9

In order to evaluate radiation resistance of the membrane of the invention, performances of the electrode obtained in Run No. 5 of Example 2 were determined after it was irradiated with gamma rays emitted from cobalt-60 at a radiation dose of $2.5 \times 10^{-5}$ R/hr for 38 hours. In this test, the inner uranyl nitrate solution was the same as used in Run No. 5, and the test solution was a $10^{-3}$M uranyl nitrate solution (pH=3). The results obtained are shown in Table 14.

TABLE 14

| | Run No. 26 | Run No. 27 |
|---|---|---|
| Responsive Membrane: | | |
| Complexing Agent | tri(chloropropyl) phosphate | tri(chloropropyl) phosphate |
| Diluent | TBP | TBP |
| Solvent Mediator | DOP | DOP |
| Irradiation Time (hr) | 0 | 38 |
| Uranyl Ion Concn. (M) | Slope (mV/decade) | Slope (mV/decade) |
| $10^{-4}$ | | |
| | 38.5 | 43.4 |
| $10^{-3}$ | | |
| | 49.4 | 43.5 |
| $10^{-2}$ | | |
| | 28.0 | 48.5 |
| $10^{-1}$ | | |
| | 26.1 | 48.6 |
| $10^{-2}$ | | |
| | 47.5 | 49.7 |
| $10^{-3}$ | | |
| | 41.0 | 44.9 |
| $10^{-4}$ | | |

EXAMPLE 10

The same test as in Example 9 was conducted for the electrode of Run No. 8 of Example 3. The results obtained are shown in Table 15.

TABLE 15

| | Run No. 28 | Run No. 29 |
|---|---|---|
| Responsive Membrane: | | |
| Complexing Agent | trioctyl phosphate | trioctyl phosphate |
| Diluent | TBP | TBP |
| Solvent Mediator | DOA | DOA |
| Irradiation Time (hr) | 0 | 38 |
| Uranyl Ion Concn. (M) | Slope (mV/decade) | Slope (mV/decade) |
| $10^{-4}$ | | |
| | 28.2 | 37.5 |
| $10^{-3}$ | | |
| | 46.6 | 45.8 |
| $10^{-2}$ | | |
| | 45.7 | 44.1 |
| $10^{-1}$ | | |
| | 45.4 | 48.2 |
| $10^{-2}$ | | |
| | 45.4 | 44.0 |
| $10^{-3}$ | | |
| | 29.2 | 35.6 |
| $10^{-4}$ | | |

It can be seen from Tables 14 and 15 that the electrodes according to the present invention only show shifts of membrane characteristics within such a range that can be calibrated even when they are exposed to radiation. In these tests, no fluctuation of the pointer of the potentiometer was observed.

As demonstrated by the foregoing examples, the present invention provides uranyl ion selective electrodes excellent in uranyl ion selectivity and concentration responsiveness. The electrodes according to the present invention also exhibit satisfactory reproducibility, accuracy, and durability and are, therefore, particularly suitable for use in uranyl ion analysis in the atomic energy industry.

While the invention has been described in detail and with reference to specific embodiments thereof, it will be apparent to one skilled in the art that various changes and modifications can be made therein without departing from the spirit and scope thereof.

What is claimed is:

1. A uranyl ion selective electrode having a responsive membrane, an inner reference electrode, and a uranyl ion inner solution, in which the responsive membrane is obtained by mixing a membrane material with an ion-exchanger comprising at least one uranyl ion complex, which is previously obtained by reacting a uranyl ion with from 2 to 3 mols, per mol of the uranyl ion, of a complexing agent which is a neutral phosphoric ester or a neutral phosphorous ester, a diluent which is a solvent for the ion-exchanger, and a solvent mediator which is a plasticizer for the membrane material with a weight ratio of said ion-exchanger to a mixture of said diluent and said solvent mediator being from 1/7 to 1/20 and a weight ratio of said diluent to said solvent mediator being form 3/1 to ½.

2. A uranyl ion selective electrode as in claim 1, wherein said membrane material is poly(vinyl chloride).

3. A uranyl ion selective electrode as in claim 1, wherein said neutral phosphoric ester or neutral phosphorous ester as a complexing agent has an alkyl or halogenated alkyl moiety having from 2 to 12 carbon atoms as an alkoxy group thereof.

4. A uranyl ion selective electrode as in claim 3, wherein said neutral phosphoric ester or neutral phosphorous ester as a complexing agent has an alkyl or halogenated alkyl moiety having from 3 to 8 carbon atoms as an alkoxy group thereof.

5. A uranyl ion selective electrode as in claim 1, wherein said diluent is a neutral phosphoric ester.

6. A uranyl ion selective electrode as in claim 5, wherein said neutral phosphoric ester has an alkyl moiety having from 2 to 12 carbon atoms as an alkoxy group thereof.

7. A uranyl ion selective electrode as in claim 6, wherein said neutral phosphoric ester has an alkyl moiety having from 3 to 8 carbon atoms as an alkoxy group thereof.

8. A uranyl ion selective electrode as in claim 1, wherein said solvent mediator which is a plasticizer for the membrane material is an ester of phthalic acid, adipic acid, or sebacic acid.

9. A uranyl ion selective electrode as in claim 8, wherein said ester has an alkyl moiety having from 2 to 12 carbon atoms as an alkoxy group thereof.

10. A uranyl ion selective electrode as in claim 9, wherein said ester has an alkyl moiety having from 3 to 8 carbon atoms as an alkoxy group thereof.

11. A uranyl ion selective electrode as in claim 1, wherein said diluent and the solvent mediator are used in a weight ratio of from 2/1 to ½.

12. A uranyl ion selective electrode as in claim 1, wherein the weight ratio of said ion-exchanger to a mixture of said diluent and solvent mediator is from ⅛ to 1/15.

13. A uranyl ion selective electrode as in claim 1, wherein the proportion of the membrane material to be mixed is from 20 to 50% by weight based on the total weight of the ion-exchanger, diluent, solvent mediator, and membrane material.

14. A uranyl ion selective electrode as in claim 13, wherein the proportion of the membrane material to be mixed is from 25 to 35% by weight based on the total weight of the ion-exchanger, diluent, solvent mediator, and membrane material.

15. A uranyl ion selective electrode as in claim 1, wherein said responsive membrane has a thickness of from 0.2 to 0.6 mm.

* * * * *